US006680193B1

(12) United States Patent
Fouillet et al.

(10) Patent No.: US 6,680,193 B1
(45) Date of Patent: Jan. 20, 2004

(54) DEVICE FOR CHEMICAL AND/OR BIOLOGICAL ANALYSIS WITH ANALYSIS SUPPORT

(75) Inventors: Yves Fouillet, Voreppe (FR); Jean-Frédéric Clerc, Le Foutauil (FR); Jean Therme, Herbeys (FR)

(73) Assignee: Commissariat a l'Energie Atomique, Paris (FR)

(*) Notice: Subject to any disclaimer, the term of this patent is extended or adjusted under 35 U.S.C. 154(b) by 0 days.

(21) Appl. No.: 09/806,515

(22) PCT Filed: Oct. 14, 1999

(86) PCT No.: PCT/FR99/02499

§ 371 (c)(1),
(2), (4) Date: May 17, 2001

(87) PCT Pub. No.: WO00/23190

PCT Pub. Date: Apr. 27, 2000

(30) Foreign Application Priority Data

Oct. 16, 1998 (FR) ........................................... 98 13012

(51) Int. Cl.[7] ............................................. C12M 1/34

(52) U.S. Cl. ................................ 435/287.2; 435/288.5

(58) Field of Search ............................ 435/91.2, 286.5, 435/287.2, 288.5

(56) References Cited

U.S. PATENT DOCUMENTS 5,589,136 A 12/1996 Northrup et al. ........... 422/102
5,716,825 A 2/1998 Hancock et al. ......... 435/286.5

FOREIGN PATENT DOCUMENTS

| | | |
|---|---|---|
| DE | 39 26 466 | 2/1991 |
| DE | 195 19 015 | 9/1996 |
| WO | WO 94/21372 | 9/1994 |
| WO | WO 96/15269 | 5/1996 |
| WO | WO 97/02357 | 1/1997 |
| WO | WO 97/04297 | 2/1997 |
| WO | WO 98/28623 | 7/1998 |
| WO | WO 98/32535 | 7/1998 |

OTHER PUBLICATIONS

Martin U. Kopp, et al., Science, vol. 280, pp. 1046–1048, "Chemical Amplification: Continuous–Flow PCR on a Chip", May 15, 1998.

Nature Biotechnology, vol. 16, p. 509, "Chips Advance But Cost Constraints Remain", Jun. 1998.

*Primary Examiner*—David A. Redding
(74) *Attorney, Agent, or Firm*—Oblon, Spivak, McClelland, Maier & Neustadt, P.C.

(57) ABSTRACT

Chemical and/or biological analysis device comprising an analysis support (100) with at least one input bowl (102) to contain a sample, at least one output bowl (104) to output the said sample, at least one internal duct (108) passing through the support to form a connection between the input bowl and the output bowl, and at least one reagent reservoir (120*a*, 120*b*, 120*c*) connected to each duct (108) between the input bowl and the output bowl, in which the input bowl, the output bowl and the reservoir open up onto a first face (106) of the analysis support.

19 Claims, 5 Drawing Sheets

DEVICE FOR CHEMICAL AND/OR BIOLOGICAL ANALYSIS WITH ANALYSIS SUPPORT

TECHNICAL FIELD

This invention relates to a chemical and/or biological analysis device equipped with an analysis support that may be of the single use type.

The invention is used in applications in chemistry and biology. In particular, the device may be used in chemical amplification processes or PCR (Polymerase Chain Reaction) type processes for the analysis of genetic material (DNA).

STATE OF PRIOR ART

Macroscopic chemical or biological analysis systems using titration plates are known. These plates comprise bowls in which samples and reagents are mixed by pipetting (with a pipette). The plates are heated to set temperatures by successive oven drying, and are then cooled, in order to enable the chemical or biological reactions.

With these systems, the addition of reagents is a long and complex operation, particularly because each reagent is added separately in turn. Furthermore, the thermal inertia involved in heating and cooling of the titration plates is too high, increasing the analysis time.

Furthermore, chemical and/or biochemical analysis equipment is known in the form of complete structures incorporating heating means necessary for analysis. Connection systems with pipes are used to input the samples and reagents into the structure.

The use of this equipment requires complex and tedious connection operations to input the fluids, analytes and reagents, and electrical connection operations to supply power to the heating equipment. Due to the specific nature of the analyses, connection operations have to be repeated every time that the equipment is used.

Furthermore, the manufacturing cost of this equipment is high.

A more complete illustration of the techniques and equipment used for biochemical analysis purposes is given in documents (1) and (2), the references of which are given at the end of this description.

PRESENTATION OF THE INVENTION

The purpose of the invention is to propose a biological and/or chemical analysis device without the limitations mentioned above.

Another purpose is to reduce heating and cooling times, and to enable a precise and selective temperature check of components to be analysed during different reaction phases.

Another purpose of the invention is to propose such a device that can quickly be adapted to different types of products to be analysed without requiring any complex connection operations.

Another purpose of the invention is to propose a single-use, very lost cost device with an analysis support, that can be thrown away and replaced after each use, or after a limited number of uses. For example, it might be possible to perform about a thousand sequential analyses with a device before throwing it away.

In order to achieve these purposes, the objective of the invention is more precisely a chemical and/or biological analysis device comprising an analysis support with at least one input bowl to collect a sample, at least one output bowl through which the said sample is returned, at least one internal duct passing through the support to connect the input bowl to the output bowl, and at least one reagent reservoir connected to each duct between an input bowl and an output bowl, in which the input bowl, the output bowl and the reservoir open up onto a first face of the analysis support.

In particular, the device may comprise several input bowls and several corresponding output bowls, each input bowl being connected to an associated output bowl through a duct.

Liquids to be analysed may be put into the input bowls and/or reagents may be put into the corresponding reservoirs by micropipetting (using a micropipette).

According to another embodiment, liquids to be analysed may be placed into the input bowls and/or the reagents may be put into the corresponding reservoirs using leak tight fluids input devices such as a lid placed on the reservoir or the bowl and connected to a syringe or a pressurized tank.

Liquids and/or reagents may be placed using a combination of the two methods described above.

For supports with a large number of bowls and/or reservoirs, the liquids to be analysed and/or the reagents may be brought in automatically by means of a high-resolution distribution (dispensing) robot. Furthermore, sequential analyses in which at least one of the reagents is replaced by another over a period may be automated by sequentially adding several different reagents into the corresponding reservoir. A neutral buffer liquid may or may not be added into the reservoir between two distinct reagents.

According to one particular aspect of the invention, the internal duct(s) may be designed to be brought close to at least a second face of the analysis support so that there is only a thin wall separating it from the said second face. In one particular embodiment, the thin wall may be less than 100 $\mu$m thick.

More precisely, the wall is chosen to be sufficiently thin to enable heat exchange with thermal sources external to the analysis support.

In particular, the wall separating the ducts from the second face may be chosen to be thinner than a wall separating ducts from each other or from the bowls.

According to another aspect of the invention, the face of the ducts opposite the thin wall may have a thermal barrier that can be made using a layer of material that does not conduct heat well and/or a substrate structure in which a cavity filled with air or a gas that is not a good heat transporter can be located on the ducts.

This thermal barrier can make the temperature in the ducts more uniform.

According to another aspect of the invention, the device may also comprise a thermal support independent of the analysis support, the thermal support comprising a heat exchange face with at least one thermal source and the said thermal support possibly being added removably onto the analysis support in order to bring the heat exchange face into contact with the second face of the analysis support.

The separate nature of the analysis support and the thermal support makes it possible to design analysis supports without their own heating or cooling means. Consequently, this characteristic can significantly reduce the cost of the analysis support. Thus, this support may be of the single use type or it may be used several times, in other words it may be thrown away after one or several uses. One use means the sequential production of a number of analyses, for example close to 1000.

The heat exchange face may comprise one or several thermostat controlled areas each equipped with at least one thermal source. The thermostat-controlled areas coincide with at least one analysis support area located on the downstream side of a connector between a reagent reservoir and a duct.

By associating a thermostat controlled area of the thermal support with a corresponding area of the analysis support located nearby, for example on the downstream side of each reagent reservoir, it would be possible to control and selectively adapt the temperature of the liquid to be analysed as a function of each reagent used.

The term downstream side used in this case is applicable to the direction of flow of liquids to be analysed starting from the input bowls and working towards the output bowls.

Thermal sources may comprise one or several thermostat controlled electric heating resistances.

Alternately, or additionally, the thermal sources may also comprise one or several ducts through which a heat transporting fluid passes. This fluid may be used to locally heat or cool the analysis support.

In one particular embodiment of the analysis support, it may be provided with a first substrate with transverse openings that form the bowls and reservoirs respectively, and a second substrate glued to the first substrate, the second substrate being provided with grooves covered by the first substrate to form ducts, and coinciding with the corresponding through openings.

This particularly simple structure can reduce manufacturing costs of the analysis supports.

The support may be manufactured according to the invention using a process comprising the following steps in sequence:

- formation of through openings in a first substrate, the said openings corresponding to an input or output bowl, or a reagent reservoir,
- formation of grooves in a second substrate, according to a pattern that joins at least two openings in the first substrate to each other,
- gluing of the first substrate onto the second substrate in order to cover the grooves,
- thinning of the second substrate after gluing, maintaining a thickness of the substrate greater than the maximum depth of the grooves.

According to one particular embodiment, the first substrate may be provided with two layers that are not good conductors of heat, for example a few microns thick.

According to a second particular embodiment, the first substrate may comprise at least one non-through opening in order to create at least one thermal insulation cavity.

The invention also relates to a process for use of the analysis device as described above, in which the analysis support is put into contact with the thermal support for a determined analysis time, at least one sample to be analysed and at least one reagent being added into the analysis support before the analysis phase starts, or during the analysis phase, and then the analysis support is removed from the thermal support after the analysis phase.

The analysis support may be reused after the end of the analysis.

Other characteristics and advantages of this invention will become clearer from the following description with reference to the figures in the attached drawings. This description is given for purely illustrative purposes and is in no way limitative.

DETAILED DESCRIPTION OF EMBODIMENTS OF THE INVENTION

Figure 1A:
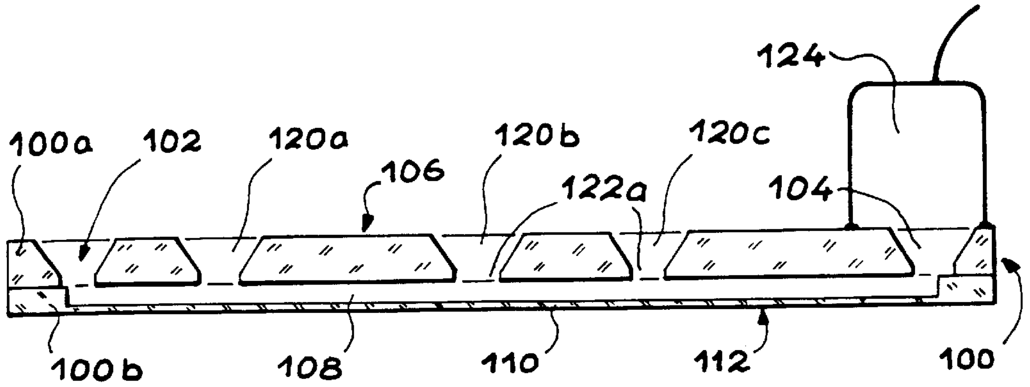
FIG. 1A is a simplified schematic section through an analysis support according to the invention.

Identical, similar or equivalent parts of the figures are marked with the same numeric references to facilitate reading in the following description.

FIG. 1 is a section through an analysis support 100 according to the invention.

This figure shows an input bowl 102 formed essentially of a through opening formed in a substrate 100*a* of the support, close to one of its ends. Similarly, an output bowl 104 is formed close to a second end. The bowls 102, 104 open up into a first face 106 of the support 100. An internal duct 108 joins the input and output bowls together.

The duct 108 is in the form of a groove etched in a second substrate 100*b* glued to the first substrate such that the latter substrate covers the groove.

It can be seen that the groove depth is practically equal to the thickness of the second substrate 100*b*, such that all that separates the duct 108 from a second face 112 of the analysis support 100 is a thin wall 110.

In the example illustrated, the support 100 is usually parallelepiped-shaped and the first and second faces are the main opposite and parallel faces.

The figure also shows a sectional view of reagent reservoirs 120*a*, 120*b*, 120*c* formed between the input bowl 102 and the output bowl 104. The reservoirs also open up onto the first face 106 of the analysis support 100. Connectors or passages 122*a* are provided to join each of the reservoirs to the duct 108.

For simplification reasons, the passages 122*a* are shown in the drawing in the figure such that the reservoirs cannot be distinguished from the input and output bowls in FIG. 1.

The liquid to be analysed may be added into the input bowls using a pipette.

The reagent reservoirs may be filled in the same way.

Figure 1B:
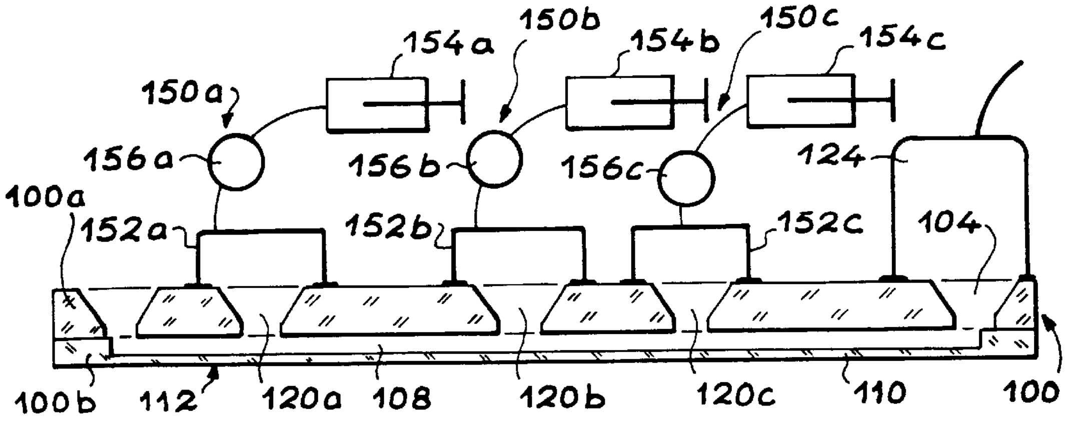
FIG. 1B shows the analysis support in FIG. 1A equipped with means of filling the reagent reservoirs.

If the sequential analysis uses different reagents in sequence, and if the reagents also need to be kept at a well controlled temperature before use, it is preferable to use small reservoirs supplied by a push-syringe type system as shown in FIG. 1B.

FIG. 1B shows an analysis support conform with FIG. 1A in which the reservoirs 120*a*, 120*b*, and 120*c* are associated with fluid input means 150*a*, 150*b* and 150*c* respectively.

These means comprise supply plugs or caps 152*a*, 152*b*, 152*c* placed above the reservoirs in a leak tight manner and connected to push-syringes 154*a*, 154*b* and 154*c* that contain the reagents. The caps may be glued to the surface of the analysis support or may be clamped in contact with the surface, and fitted with a seal.

References 156*a*, 156*b* and 156*c* denote pressure sensors formed on ducts connecting the push-syringes to caps 152*a*, 152*b* and 152*c* respectively, in order to control the pressure and/or flow of reagents.

Although it is not shown, a similar feed system may also be used on the input bowls.

As shown in FIGS. 1A and 1B, atmospheric pressure is applied to the input bowls and the reservoirs, or they may be pressurized at a pressure fixed by the feed system, while a vacuum line 124 is applied to the output bowls.

An initial spontaneous filling of the analysis support may be made with a polar solvent (such as alcohol) followed by a nominal solvent in order to prevent the formation of bubbles. This filling makes use of a capillarity effect in the ducts.

The analytes and reagents are added after this first filling.

The analysis product arriving at the output bowls may also be sampled using pipettes.

Figure 2:
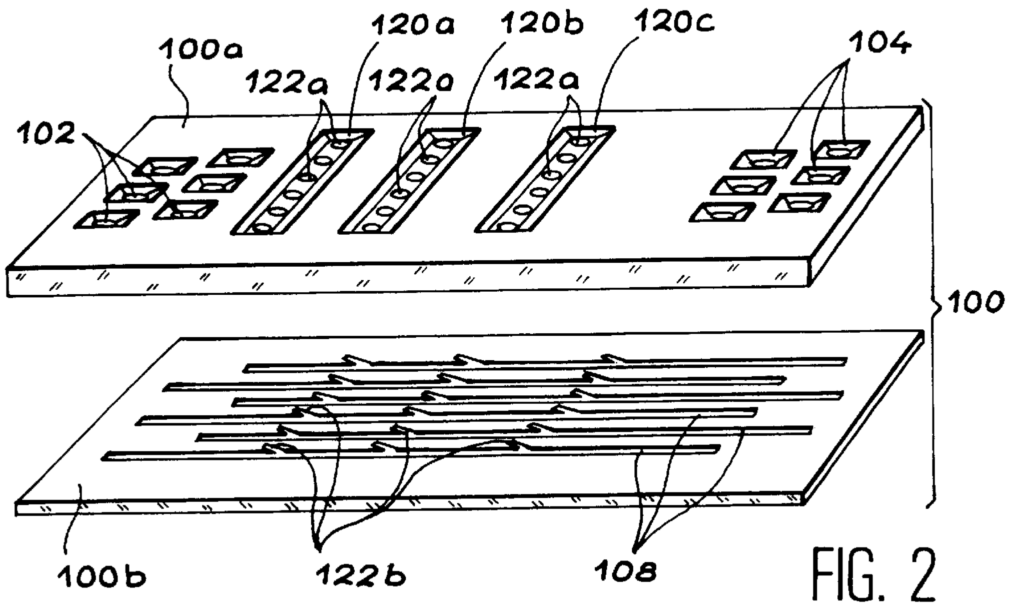
FIG. 2 is an exploded perspective view more precisely showing the structure of the analysis support.

FIG. 2 shows the two substrates 100*a* and 100*b* that form the analysis support more precisely and separately.

It can be seen that the analysis support comprises several input bowls 102 and several output bowls 104.

The bowls are in the form of through openings formed in the first substrate 100*a*. These openings are in the form of a flared V forming a funnel.

Furthermore, in the example shown in FIG. 2, each input bowl 102 is connected individually to an output bowl 104 through a duct 108.

The analysis support comprises three reagent reservoirs 120*a*, 120*b* and 120*c*.

In this example, each reservoir is common to several ducts 108, and it is connected to the ducts by means of connectors 122*a* and 122*b*. More precisely, reference 122*a* denotes drillings in the first substrate 110*a* connecting a reservoir to the corresponding branch connections 122*b* formed in the second substrate 110*b* and connected to each of the corresponding ducts (obviously, an individual reservoir may also be provided for each of the different ducts).

The quantities of liquids (liquids to be analysed and reagents) that are mixed at the intersection of branch connections 122*b* and ducts 108 depend on the size of each of these branch connections and ducts 108.

Figure 3:
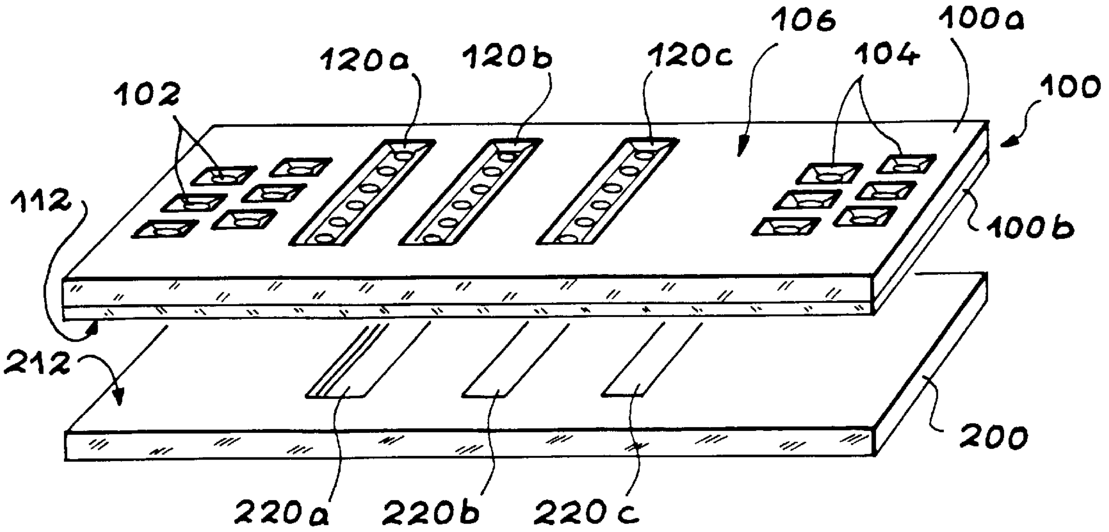
FIG. 3 is a simplified perspective view of an analysis support according to FIG. 2, shown with a thermal support.

FIG. 3 shows an analysis support 100 conform with that shown in FIG. 2, in which the substrates 100*a* and 100*b* are permanently glued.

The analysis support is shown above a corresponding thermal support 200.

The thermal support 200 has a heat exchange face 212 facing the second face 112 of the analysis support 100, close to which the ducts are located. The heat exchange face 212 of the thermal support 200 and the second face 112 of the analysis support are designed to come into contact with each other.

The heat exchange face 212 has three thermostat controlled areas 220*a*, 220*b* and 220*c* each equipped with one or several thermal sources (not shown).

The three thermostat controlled areas 220*a*, 220*b*, 220*c* are laid out to coincide with portions of the analysis support ducts located close to the reservoirs 120*a*, 120*b* and 120*c* respectively, or more precisely the branch connections through which the reagents are added.

Figure 5:
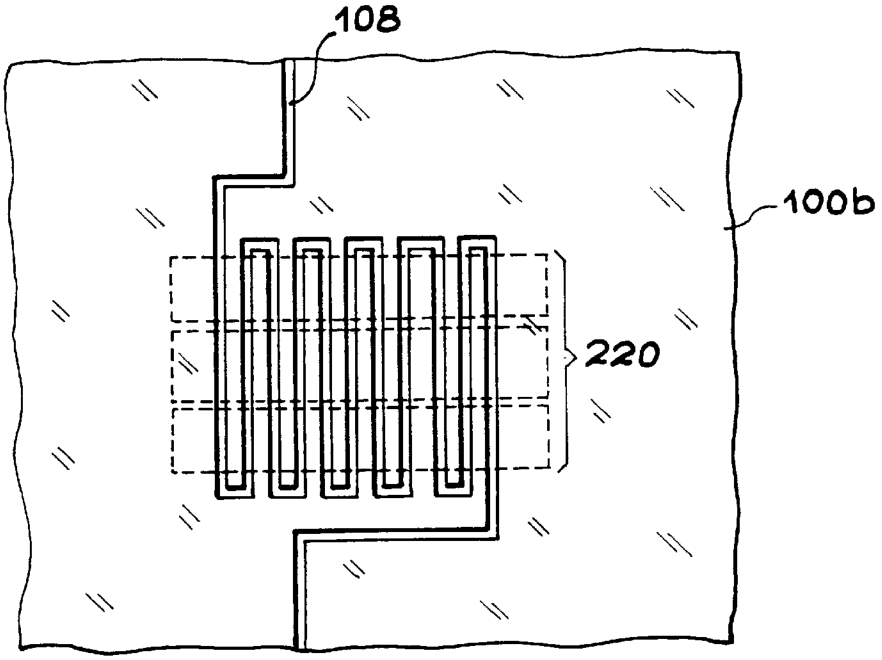
FIG. 5 is a plan view of part of an analysis support according to the invention, forming a variant to FIGS. 1 to 4.

The fluid in the duct 122*b* may pass through each heating area once or several times, by the use of adapted duct patterns as shown in FIG. 5 described later.

Figure 4:
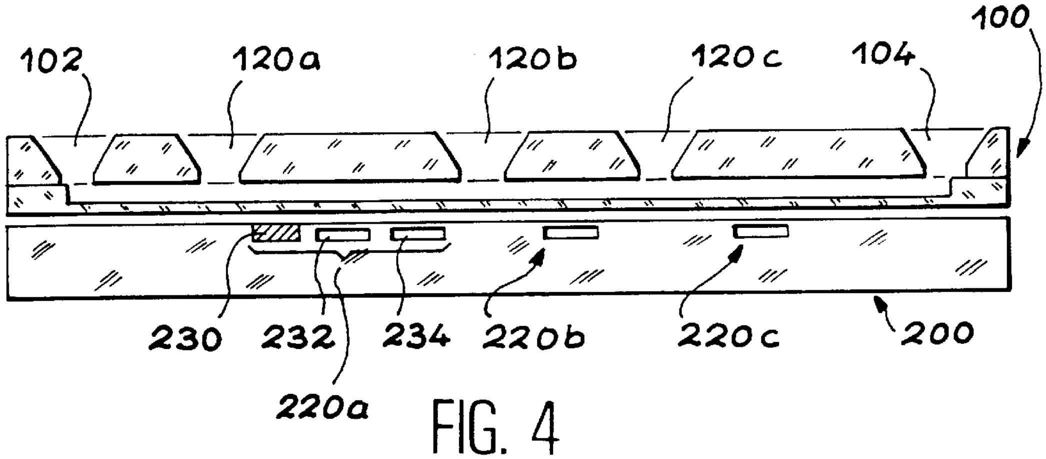
FIG. 4 is a schematic longitudinal section through the analysis support placed on the thermal support.

FIG. 4 is a schematic section through the analysis support transferred onto to thermal support showing a more detailed view of the thermostat-controlled areas.

For reasons of clarity in the figure, the analysis support and the thermal support are shown slightly separated from each other. However, these supports are in contact with each other.

As described above, the thermostat-controlled areas may comprise several thermal sources. This is the case of the thermostat controlled area 220*a*. This area comprises a first thermal source 230 formed of electrical resistances, for example such as platinum micro-resistances. It also comprises two sources 232 and 234 in the form of ducts through which heat-transporting fluids can pass.

In the case of a PCR type analysis, the electrical resistances of the first source 230 may be increased to a temperature of 94° C., the heat transporting fluid of the second thermal source 232 may be increased to a temperature of 55° C. and the heat transporting fluid of the third thermal source 234 may be increased to a temperature of 72° C.

These temperatures correspond to DNA denaturisation, hybridisation and elongation steps (see document (1)).

The thermal sources may be miniaturised such that the thermal resolution of the thermal support is less than one millimetre.

FIG. 5 shows a top view of part of a first substrate 100*a* of an analysis support and shows a variant embodiment of a duct 108.

The duct 108 is folded according to a repeated geometric pattern.

The figure also includes a discontinuous line showing the position of thermal sources in a thermostat-controlled area 200 of a thermal support that can be associated with the analysis support. It can be seen that a liquid to be analysed can come into thermal contact with different thermal sources in the thermostat-controlled area in sequence, passing through the different segments of the geometric pattern of the duct.

Figure 6:
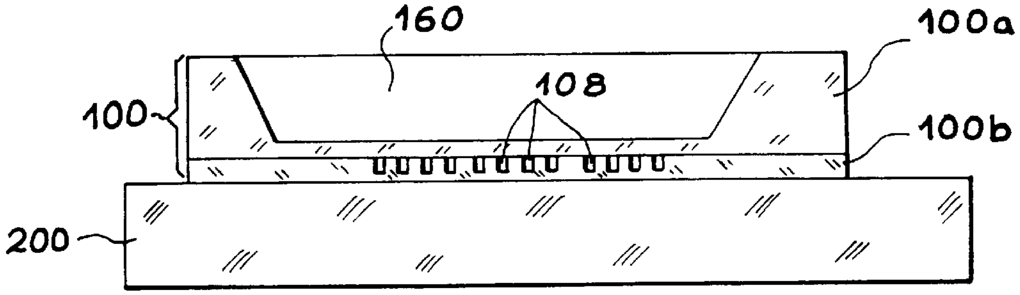
FIG. 6 is a simplified cross section through an analysis support including a part conform with FIG. 5.
Figure 7:
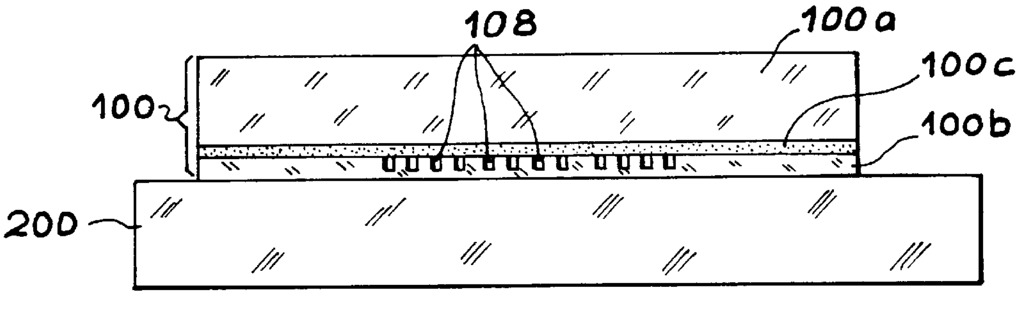
FIG. 7 is a simplified cross section through an analysis support including a part conform with FIG. 5 and forming a variant to FIG. 6, FIGS. 8, 9, 10 and 11 are schematic longitudinal sections of substrates during successive steps in the manufacture of an analysis support according to the invention.

FIGS. 6 and 7 show two variant embodiments of the device to improve the uniformity of the temperature in the ducts by isolating their upper face, in other words the face opposite the said second face 112 of the analysis support. A first solution shown in FIG. 6 consists of making a cavity 160 (opening or not opening to the surface) in the upper part 100*a* of the hybridisation support. This cavity coincides with at least part of the duct 108. A second solution shown in FIG. 7 consists of placing a layer 100*c* of a material that is a poor conductor of heat, between the upper and lower parts 100*a*, 100*b* of the analysis support. It is also possible to use an upper substrate equipped with a layer 100*c* of a thermal insulating material.

FIGS. 8 to 11 described below show an example of a manufacturing process for an analysis support as described above.

Figure 8:
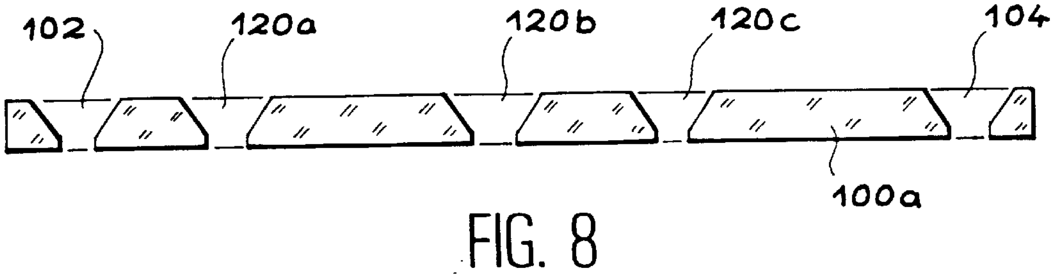

In the first substrate plate 100*a*, for example made of silicon, through openings are formed as shown in FIG. 8. These openings form bowls or reservoirs 102, 104, 120*a*, 120*b*, 120*c*. The openings are etched chemically, and are made with inclined sides by anisotropic chemical etching, for example (KOH) in order to give them a flared shape. The location of the openings is defined by an etching mask (not shown) coincident with the pattern of grooves. For example, the penetration through the layer 100*c* of the thermal insulating material, for example $SiO_2$ in the case of the variant shown in FIG. 7, may be done by $CHF_3$ etching by a dry method, the dimension of the perforation being defined by an etching mask or by using the walls of the hole created by chemical etching as a mask.

Figure 9:
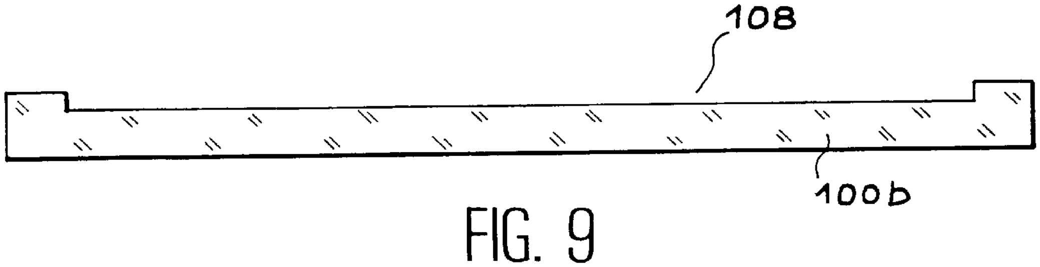

FIG. 9 shows etching of the grooves forming the ducts 108 in a second substrate 100*b*, for example made of silicon. Etching is done through an etching mask (not shown) with a pattern corresponding to the required ducts. For example, chemical etching (KOH) may be used. The depth of the grooves may for example be of the order of 100 μm for a substrate 100*b* with a thickness between 250 and 450 μm.

Dry SG6 etching may also be used in order to make grooves with a depth greater than their width, for example 100 μm×20 μm.

Figure 10:
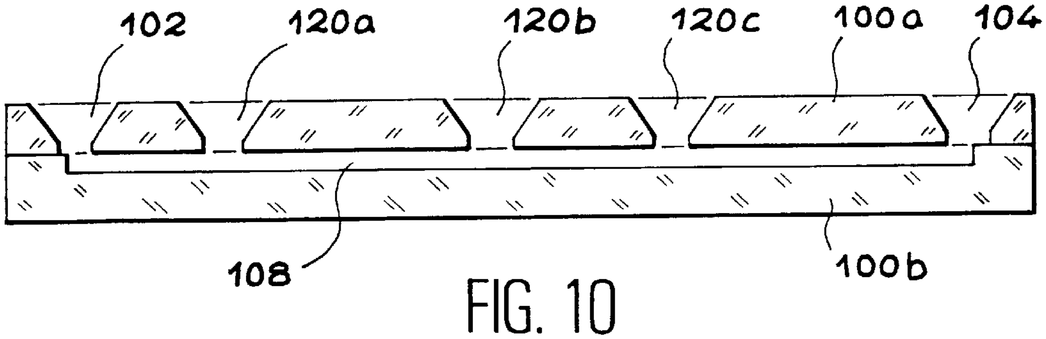

A third step shown in FIG. 10 consists of sealing the first and second substrates 100*a* and 100*b* in order to put the bowls or reservoirs 102, 104, 120*a*, 120*b*, 120*c* into communication with the ducts (grooves) 108 corresponding to them. For example, sealing may be done by direct (molecular) gluing of the two substrates.

During this operation, the grooves 108 of the second substrate 100*b* are covered by the first substrate 100*a* to form ducts.

Figure 11:
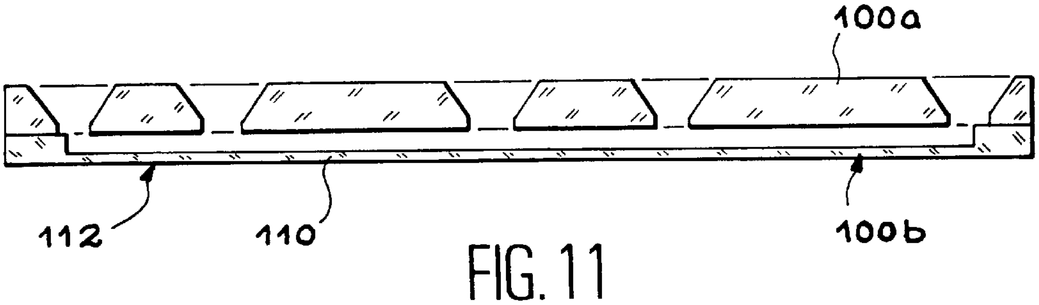

A final step shown in FIG. 11 consists of thinning the second substrate 100*b* to preserve only a thin wall 110 between the duct 108 and the outer surface 112.

This wall 110 is 10 μm thick, to facilitate heat exchanges.

Thinning is achieved by etching and/or mechanochemical polishing.

Several analysis supports conform with the invention may be made simultaneously and collectively using the above process in two silicon wafers (corresponding to the first and second substrates).

In this case, the process is terminated by cutting the wafers with a saw to separate individual analysis supports.

Figure 12:
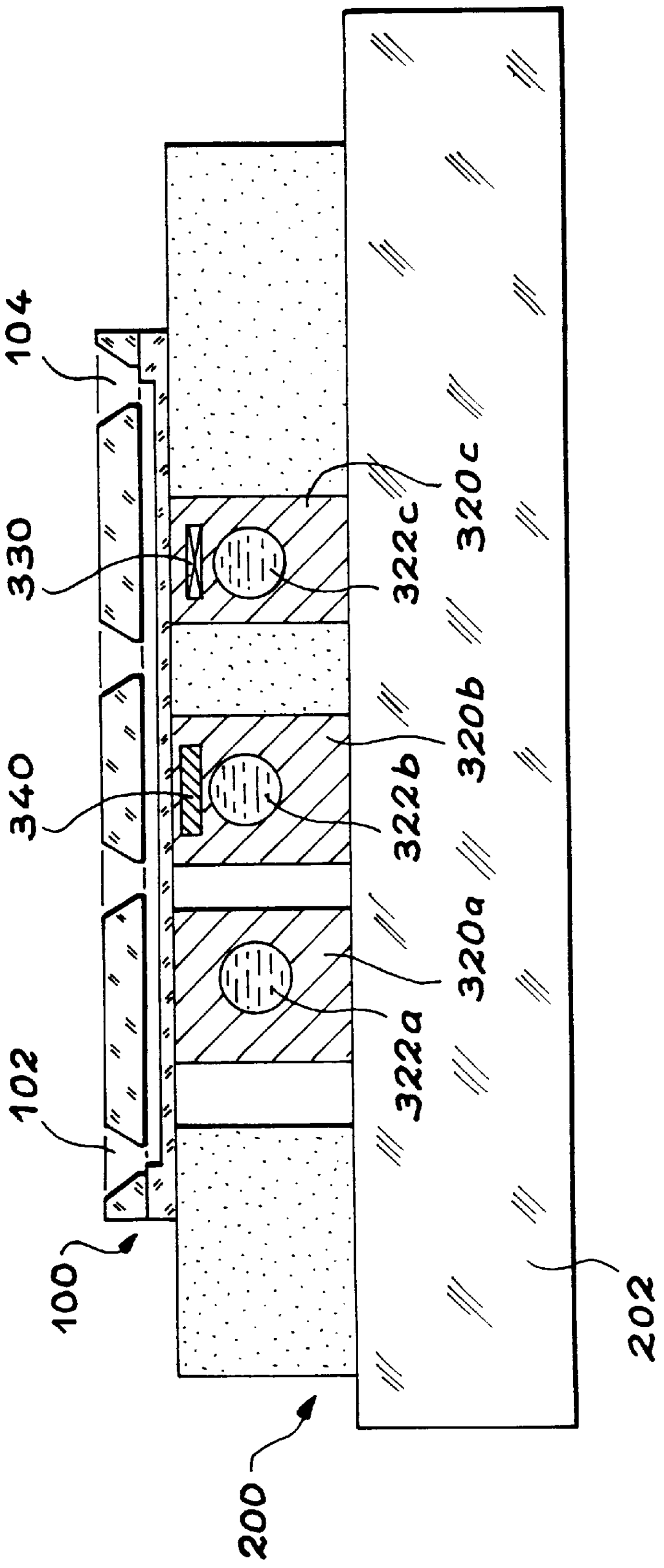
FIG. 12 is a cross section through an analysis support and a thermal support according to the invention and illustrates a particular embodiment of the thermal support.

FIG. 12 shows a particular embodiment of the thermal support 200 of an analysis device according to the invention.

Essentially, the thermal support 200 comprises a base 202 on which one or several thermostat controlled strips are laid out. In the example shown in the figure, the thermal support comprises three thermostat controlled strips 320*a*, 320*b*, 320*c* that form three thermostat controlled areas respectively.

All or part of the strips may be embedded in a thermal insulating material. In the example shown in the figure, two strips 320*b* and 320*c* are surrounded by a solid thermal insulating material, whereas the first strip 320*a* is left in free contact with ambient air on its side faces.

Each strip is provided with heating and/or cooling means.

The first strip 320*a* is provided with a duct 322*a* that passes through it and controls its temperature by circulating a heat transporting fluid.

The other strips 320*b* and 320*c* are also provided with similar ducts 322*b* and 322*c*. Ducts are connected to thermostat-controlled baths with pumping systems (not shown) to circulate the heat transporting fluid.

The connection between the baths and the strips may be made using hydraulic connection means not shown.

Ducts may be circular as shown in the figures, but may also be provided with rib systems to optimise heat exchanges.

Additional heating elements may be included in the strips. For example, the third strip 320*c* is equipped with an electrical resistance 330. In this case, the electrical resistance is used as a "heating source" whereas the heat transporting fluid is used as a "cooling source".

The second strip 320*b* comprises a temperature measurement element 340 such as a resistance, for example used to servocontrol the temperature of the associated thermostat controlled bath.

The reference 100 generally denotes a removable analysis support located on the thermal support to come into contact with the thermostat-controlled strips. A detailed description of this support is not given here. For further information, refer to the explanations given with reference to the previous figures. The analysis support 100 may simply be placed on the thermal support 200. It may also be pressed into contact with the thermal support by means of a flange or a suction system not shown.

The analysis support is simple and inexpensive to make, because the means provided for temperature control, in other words in particular the thermostat controlled baths and thermostat controlled strips, are fixed to the thermal support or are connected to the thermal support through fluids, and because the analysis support is removable.

DOCUMENTS MENTIONED (1)

Martin U Kopp et al.

"Chemical Amplification: continuous-Flow PCR on a chip",

Science, vol. 280, May 15 1998, pages 1046–1048.

(2)

"Chip advance but cost constraints remain"in Nature Biotechnology, vol. 16, June 1998, page 509.

What is claimed is:

1. A chemical and/or biological analysis device comprising:

an analysis support with at least one input bowl to collect a sample, at least one output bowl to output the sample, at least one internal duct passing through the analysis support to connect the at least one input bowl and the at least one output bowl, and at least one reagent reservoir connected to each duct between the at least one input bowl and the at least one output bowl, in which the at least one input bowl, the at least one output bowl and the at least one reagent reservoir open up onto a first face of the analysis support, in which the at least one internal duct extends close to at least one second face of the analysis support so that the at least one internal duct is separated from the at least one second face by a thin wall; and a thermal support independent of the analysis support the thermal support having one heat exchange face with at least one thermostat controlled area provided with at least one thermal source;

wherein the analysis support is added removably onto the thermal support to put the heat exchange face of the thermal support into contact with the at least one second face of the analysis support.

2. A chemical and/or biological analysis device according to claim 1, further comprising a thermal barrier placed on one side of the at least one internal duct opposite the at least one second face of the analysis support.

3. A chemical and/or biological analysis device according to claim 2, wherein the thermal barrier comprises a thermal insulation layer above the at least one internal duct.

4. A chemical and/or biological analysis device according to claim 2, wherein the thermal barrier comprises a thermal insulation cavity above the at least one internal duct.

5. A chemical and/or biological analysis device according to claim 1, wherein the thin wall is less than 100 $\mu$m thick.

6. A chemical and/or biological analysis device according to claim 1, wherein the thermostat controlled area coincides with at least one analysis support area located close to a connector between the at least one reagent reservoir and at least one internal duct, when the analysis support is transferred onto the thermal support.

7. A chemical and/or biological analysis device according to claim 1, wherein the thermal support comprises cooling means and/or heating means.

8. A chemical and/or biological analysis device according to claim 7, wherein the heating means comprise at least one electrical resistance.

9. A chemical and/or biological analysis device according to claim 7, wherein the cooling means and/or the heating means comprise at least one heat transporting fluid duct.

10. A chemical and/or biological analysis device according to claim 1, wherein the at least one input bowl, output bowl, and internal duct comprise a plurality of input bowls and a plurality of output bowls connected through a plurality of internal ducts, respectively.

11. A chemical and/or biological analysis device according to claim 10, wherein the at least one reagent reservoir comprises a plurality of reagent reservoirs, each being connected to each of the plurality of internal ducts.

12. A chemical and/or biological analysis device according to claim 11, further comprising external filling means for filling the plurality of reagent reservoirs, and at least one push syringe with or without a reagent mixer, connected in a leak tight manner to at least one of the plurality of reagent reservoirs.

13. A chemical and/or biological analysis device according to claim 12, wherein the external filling means comprise feed caps covering the plurality of reagent reservoirs in a leak tight manner and each equipped with at least one duct connected to a corresponding push-syringe.

14. A chemical and/or biological analysis device according to claim 1, wherein the analysis support comprises a first substrate with through openings that form the at least one input and output bowls and at least one reagent reservoir, respectively, and a second substrate glued to the first substrate, the second substrate having grooves covered by the first substrate to form the at least one internal duct and coinciding with the through openings.

15. A process for manufacturing an analysis support, comprising:

forming through openings in a first substrate, each of the through openings corresponding to an input or output bowl, or a reagent reservoir;

forming grooves in a second substrate according to a pattern that joins at least two of the through openings in the first substrate;

gluing the first substrate to the second substrate so as to cover the grooves; and thinning the second substrate after the gluing, such that the thickness of the substrate remains greater than the maximum depth of the grooves.

16. A process for use of the chemical and/or biological analysis device according to claim 1, wherein the analysis support is put into contact with the thermal support for a determined analysis time, at least one sample to be analyzed and at least one reagent being added into the analysis support before the analysis phase starts, or during the analysis phase, and then the analysis support is removed from the thermal support after the analysis phase.

17. A process for manufacturing an analysis support according to claim 15, wherein the thinning comprising etching.

18. A process for manufacturing an analysis support according to claim 15, wherein the thinning comprising mechanochemical polishing.

19. A chemical and/or biological analysis support for a chemical and/or biological analysis device, comprising:

at least one input bowl configured to collect a sample;

at least one output bowl configured to output the sample;

at least one internal duct passing through the analysis support connecting the at least one input bowl and the at least one output bowl; and at least one reagent reservoir connected to the at least one internal duct between the at least one input bowl and the at least one output bowl, wherein the at least one input bowl, at least one output bowl and at least one reagent reservoir are opened up to a first face of the analysis support, and the at least one internal duct extending sufficiently close to at least one second face of the analysis support such that the at least one internal duct is separated from the at least one second face by a wall configured to be attached to a thermal support which is independent of the analysis support and has one heat exchange face with at least one thermostat controlled area provided with at least one thermal source.

* * * * *